(12) United States Patent
Blackford et al.

(10) Patent No.: US 8,710,159 B2
(45) Date of Patent: Apr. 29, 2014

(54) POLYFUNCTIONAL SULFUR-CONTAINING EPOXIES AND COMPOSITIONS THEREOF

(75) Inventors: Timothy Blackford, Sherman Oaks, CA (US); Juexiao Cai, Stevenson Ranch, CA (US); Raquel Keledjian, Glendale, CA (US); Renhe Lin, Stevenson Ranch, CA (US); Jose Luzano, Los Angeles, CA (US); Chandra B. Rao, Valencia, CA (US); Bruce Virnelson, Valencia, CA (US)

(73) Assignee: PRC DeSoto International, Inc., Sylmar, CA (US)

( * ) Notice: Subject to any disclaimer, the term of this patent is extended or adjusted under 35 U.S.C. 154(b) by 7 days.

(21) Appl. No.: 13/529,208

(22) Filed: Jun. 21, 2012

(65) Prior Publication Data

US 2013/0345372 A1    Dec. 26, 2013

(51) Int. Cl.
 C08G 75/04    (2006.01)
 C08G 75/14    (2006.01)
 C08L 81/02    (2006.01)

(52) U.S. Cl.
 USPC .............. 525/535; 528/375; 277/316; 156/60

(58) Field of Classification Search
 USPC .............. 525/535; 528/375; 277/316; 156/60
 See application file for complete search history.

(56) References Cited

U.S. PATENT DOCUMENTS

| | | | |
|---|---|---|---|
| 4,104,283 A * | 8/1978 | Hickner | 549/556 |
| 4,366,307 A | 12/1982 | Singh et al. | |
| 4,609,762 A | 9/1986 | Morris et al. | |
| 4,623,711 A | 11/1986 | Morris et al. | |
| 5,225,472 A | 7/1993 | Cameron et al. | |
| 6,172,179 B1 | 1/2001 | Zook et al. | |
| 6,509,418 B1 * | 1/2003 | Zook et al. | 525/212 |
| 6,525,168 B2 | 2/2003 | Zook et al. | |
| 2005/0010003 A1 * | 1/2005 | Sawant et al. | 525/523 |
| 2006/0270796 A1 | 11/2006 | Sawant et al. | |
| 2007/0287810 A1 | 12/2007 | Rao et al. | |
| 2009/0326167 A1 * | 12/2009 | Sawant et al. | 525/529 |
| 2010/0010133 A1 | 1/2010 | Zook et al. | |
| 2010/0036063 A1 | 2/2010 | Sawant et al. | |
| 2010/0041839 A1 | 2/2010 | Anderson et al. | |

* cited by examiner

Primary Examiner — Randy Gulakowski
Assistant Examiner — Christopher M Rodd
(74) Attorney, Agent, or Firm — William Lambert

(57) ABSTRACT

Disclosed are polyfunctional sulfur-containing epoxies and compositions containing polyfunctional sulfur-containing epoxies. The polyfunctional sulfur-containing epoxies may be used as a curing agent and combined with polythioethers and/or polysulfides used to provide high elongation sealants useful in aerospace applications.

12 Claims, No Drawings

POLYFUNCTIONAL SULFUR-CONTAINING EPOXIES AND COMPOSITIONS THEREOF

FIELD

The present disclosure relates to polyfunctional sulfur-containing epoxies and compositions comprising the polyfunctional sulfur-containing epoxies. The disclosed polyfunctional sulfur-containing epoxies may be used as curing agents and combined with polythioethers and/or polysulfides to provide sealants useful in aerospace applications.

BACKGROUND

Epoxy curing agents are used to cure thiol-terminated sulfur-containing polymers such as polythioethers and polysulfides. Examples of such systems are disclosed in U.S. Publication Nos. 2005/0010003, 2006/0270796, 2007/0287810, 2009/0326167, and 2010/036063. These systems are useful as sealants and can meet the demanding performance requirements of the aerospace industry.

It is desirable that the weight of components used in aviation vehicles be reduced, when possible. As sealants are used throughout an aviation vehicle, a significant decrease in weight can be realized by using low-density sealants. It is well known that the weight of a sealant, coating, or other composition can be reduced by the introduction of low-density fillers. However, the inclusion of additional fillers in a polymeric composition can reduce, disrupt, and/or otherwise affect the network of the cured polymer such that the performance of the cured composition is compromised, especially upon exposure to fuel. For example, in certain epoxy-cured sulfur-containing polymer compositions, the addition of low-density fillers can reduce the elongation of the cured composition.

SUMMARY

As a result, it is desirable to provide low-density, epoxy-curable sulfur-containing polymer compositions having enhanced performance including physical properties such as increased elongation. To accomplish this objective, polyfunctional sulfur-containing epoxies are provided that when used as a curing agent in low-density compositions, provide increased elongation, and in particular increased elongation following exposure to aviation fuel.

In a first aspect, polyfunctional sulfur-containing epoxies are provided comprising the reaction products of reactants comprising: (a) a polyfunctional compound having at least three terminal groups reactive with a thiol group; (b) a dithiol; and (c) an epoxide comprising an epoxy group and a group that is reactive with a thiol group; wherein the polyfunctional sulfur-containing epoxy has a molecular weight from 500 Daltons to 3,000 Daltons.

In a second aspect, polyfunctional sulfur-containing epoxies of Formula (1) are provided:

  (1)

wherein
  each $R^1$ is independently selected from $C_{2-6}$ alkanediyl, $C_{6-8}$ cycloalkanediyl, $C_{6-10}$ alkanecycloalkanediyl, $C_{5-8}$ heterocycloalkanediyl, and $-[-(CHR^3)_s-X-]_q-(CHR^3)_r-$;
  wherein:
    each $R^3$ is independently selected from hydrogen and methyl;
    each X is independently selected from $-O-$, $-S-$, and $-NR-$ wherein R is selected from hydrogen and methyl;
    s is an integer from 2 to 6;
    q is an integer from 1 to 5; and
    r is an integer from 2 to 10;
  each -A' represents a moiety formed by the reaction of compound A with a thiol group, wherein compound A is an epoxide comprising an epoxy group and a group that is reactive with a thiol group;
  B represents a core of a z-valent, polyfunctional compound $B(-V)_z$, wherein:
    z is an integer from 3 to 6; and
    each $-V$ is a moiety comprising a terminal group that is reactive with a thiol group; and
  each $-V'-$ represents a moiety formed by the reaction of each $-V$ with a thiol group.

In a third aspect, polyfunctional sulfur-containing epoxies are provided that comprise the reaction products of reactants comprising (a) a polyfunctional compound having at least three terminal groups reactive with a thiol group; (b) a dithiol; and (c) an epoxide comprising an epoxy group and a group that is reactive with a thiol group.

In a fourth aspect, compositions comprising (a) a sulfur-containing polymer; and (b) a curing agent comprising a polyfunctional sulfur-containing epoxy provided by the present disclosure are disclosed.

In a fifth aspect, cured sealants comprising a composition comprising a polyfunctional sulfur-containing epoxy provided by the present disclosure are disclosed.

In a sixth aspect, apertures sealed with a sealant comprising a composition comprising a polyfunctional sulfur-containing epoxy provided by the present disclosure are disclosed.

In a seventh aspect, methods of sealing an aperture are disclosed comprising: (a) applying a sealant comprising a composition provided by the present disclosure to at least one surface defining the aperture; (b) assembling the surfaces defining the aperture; and (c) curing the sealant to provide the sealed aperture.

DETAILED DESCRIPTION

Definitions

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments provided by the present disclosure are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. In addition, in this application, the use of "or" means "and/or" unless specifically stated otherwise, even though "and/or" may be explicitly used in certain instances.

A dash ("-") that is not between two letters or symbols is used to indicate a point of bonding for a substituent or between two atoms. For example, —CONH$_2$ is bonded to another chemical moiety through the carbon atom.

"Alkanediyl" refers to a diradical of a saturated, branched or straight-chain, acyclic hydrocarbon group, having, for example, from 1 to 18 carbon atoms ($C_{1-18}$), from 1-14 carbon atoms ($C_{1-14}$), from 1-6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. In certain embodiments, the alkanediyl is $C_{2-14}$ alkanediyl, $C_{2-10}$ alkanediyl, $C_{2-8}$ alkanediyl, $C_{2-6}$ alkanediyl, $C_{2-4}$ alkanediyl, and in certain embodiments, $C_{2-3}$ alkanediyl. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. In certain embodiments, each cycloalkyl and/or cycloalkanediyl group(s) is $C_{3-6}$, $C_{5-6}$, and in certain embodiments, cyclohexyl or cyclohexanediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanecycloalkane group is $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, and in certain embodiments, $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. In certain embodiments, the alkanecycloalkanediyl group is $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, and in certain embodiments, $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkenyl" group refers to a group (R)$_2$C═C(R)$_2$ or —RC═C(R)$_2$ where the alkenyl group is a terminal group and is bonded to a larger molecule. In such embodiments, each R may be selected from, for example, hydrogen and $C_{1-3}$ alkyl. In certain embodiments, each R is hydrogen and an alkenyl group has the structure —CH═CH$_2$.

"Alkoxy" refers to a —OR group where R is alkyl as defined herein. Examples of alkoxy groups include methoxy, ethoxy, n-propoxy, isopropoxy, and n-butoxy. In certain embodiments, the alkoxy group is $C_{1-8}$ alkoxy, $C_{1-6}$ alkoxy, $C_{1-4}$ alkoxy, and in certain embodiments, $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. In certain embodiments, the alkyl group is $C_{2-6}$ alkyl, $C_{2-4}$ alkyl, and in certain embodiments, $C_{2-3}$ alkyl. Examples of alkyl groups include methyl, ethyl, n-propyl, iso-propyl, n-butyl, iso-butyl, tert-butyl, n-hexyl, n-decyl, tetradecyl, and the like. In certain embodiments, the alkyl group is $C_{2-6}$ alkyl, $C_{2-4}$ alkyl, and in certain embodiments, $C_{2-3}$ alkyl.

"Cycloalkanediyl" refers to a diradical saturated monocyclic or polycyclic hydrocarbon group. In certain embodiments, the cycloalkanediyl group is $C_{3-12}$ cycloalkanediyl, $C_{3-8}$ cycloalkanediyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. In certain embodiments, the cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

"Heteroalkanediyl" refers to an alkanediyl group in which one or more of the carbon atoms are replaced with a heteroatom, such as N, O, S, or P. In certain embodiments of heteroalkanediyl, the heteroatom is selected from N and O.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

A "Michael acceptor" refers to an activated alkene, such as an alkenyl group proximate to an electron-withdrawing group such as a ketone, nitro, halo, nitrile, carbonyl, or nitro group. Michael acceptors are well known in the art. A "Michael acceptor group" refers to an activated alkenyl group and an electron-withdrawing group. In certain embodiments, a Michael acceptor group is selected from a vinyl ketone, a vinyl sulfone, a quinone, an enamine, a ketimine, an aldimine, an oxazolidine, and an acrylate. In certain embodiments, a Michael acceptor group is derived from a vinyl ketone and has the structure of Formula (2):

$$—S(O)_2—C(R)_2═CH_2 \qquad (2)$$

where each R is independently selected from hydrogen, fluorine, and $C_{1-3}$ alkyl. In certain embodiments, each R is hydrogen. In certain embodiments, a Michael acceptor or Michael acceptor group does not encompass acrylates. A "Michael acceptor compound" refers to a compound comprising at least one Michael acceptor. In certain embodiments, a Michael acceptor compound is divinyl sulfone, and a Michael acceptor group is vinylsulfonyl (—S(O)$_2$—CH$_2$═CH$_2$).

As used herein, "polymer" refers to oligomers, homopolymers, and copolymers. Unless stated otherwise, molecular weights are number average molecular weights for polymeric materials indicated as "Mn" as determined, for example, by gel permeation chromatography using a polystyrene standard in an art-recognized manner.

"Substituted" refers to a group in which one or more hydrogen atoms are each independently replaced with the same or different substituent(s). In certain embodiments, the substituent is selected from halogen, —S(O)$_2$OH, —S(O)$_2$, —SH, —SR where R is $C_{1-6}$ alkyl, —COOH, —NO$_2$, —NR$_2$ where each R is independently selected from hydrogen and $C_{1-3}$ alkyl, —CN, =O, $C_{1-6}$ alkyl, —CF$_3$, —OH, phenyl, $C_{2-6}$ heteroalkyl, $C_{5-6}$ heteroaryl, $C_{1-6}$ alkoxy, and —COR where R is $C_{1-6}$ alkyl. In certain embodiments, the substituent is chosen from —OH, —NH$_2$, and $C_{1-3}$ alkyl.

Reference is now made to certain embodiments of polyfunctional epoxies, polymers, compositions, and methods. The disclosed embodiments are not intended to be limiting of the claims. To the contrary, the claims are intended to cover all alternatives, modifications, and equivalents.

Polyfunctional Sulfur-Containing Epoxies

In certain embodiments, polyfunctional sulfur-containing epoxies provided by the present disclosure have the structure of Formula (1):

$$B(-V'-S-R^1-S-A')_z \qquad (1)$$

wherein
each $R^1$ is independently selected from $C_{2-6}$ alkanediyl, $C_{6-8}$ cycloalkanediyl, $C_{6-10}$ alkanecycloalkanediyl, $C_{5-8}$ heterocycloalkanediyl, and —[—(CHR$^3$)$_s$—X—]$_q$—(CHR$^3$)$_r$—; wherein:
  each $R^3$ is independently selected from hydrogen and methyl;
  each X is independently selected from —O—, —S—, and —NR— wherein R is selected from hydrogen and methyl;
  s is an integer from 2 to 6;
  q is an integer from 1 to 5; and
  r is an integer from 2 to 10;
each -A' represents a moiety formed by the reaction of compound A with a thiol group, wherein compound A is an epoxide comprising an epoxy group and a group that is reactive with a thiol group;
B represents a core of a z-valent, polyfunctional compound B(—V)$_z$, wherein:
  z is an integer from 3 to 6; and
  each —V is a moiety comprising a terminal group that is reactive with a thiol group; and
each —V'— represents a moiety formed by the reaction of each —V with a thiol group.

In certain embodiments, $R^1$ is selected from $C_{2-6}$ alkanediyl and —[—(CHR$^3$)$_s$—X—]$_q$—(CHR$^3$)$_r$—.

In certain embodiments, $R^1$ is —[—(CHR$^3$)$_s$—X—]$_q$—(CHR$^3$)$_r$—, and in certain embodiments X is —O— and in certain embodiments, X is —S—.

In certain embodiments, where $R^1$ is —[—(CHR$^3$)$_s$—X—]$_q$—(CHR$^3$)$_r$—, p is 2, r is 2, q is 1, and X is —S—; in certain embodiments, p is 2, q is 2, r is 2, and X is —O—; in certain embodiments, p is 2, r is 2, q is 1, and X is —O—.

In certain embodiments, where $R^1$ is —[—(CHR$^3$)$_s$—X—]$_q$—(CHR$^3$)$_r$—, each $R^3$ is hydrogen, and in certain embodiments, at least one $R^3$ is methyl.

In certain embodiment of a compound of Formula (1), each $R^1$ is the same, and in certain embodiments, at least one $R^1$ is different.

A' is derived from the reaction of compound A with a thiol group, where A is an epoxide comprising an epoxy group and a group that is reactive with a thiol group. Examples of groups that are reactive with a thiol group include an alkenyl group, an epoxy group, and a Michael acceptor group.

Examples of compounds having an alkenyl group and an epoxy group include allyl glycidyl ether, 1,2-epoxy-5-hexene, 1,2-epoxy-7-octene, 1,2-epoxy-9-decene, 4-vinyl-1-cyclohexene 1,2-epoxide, butadiene monoepoxide, isoprene monoepoxide, and limonene monoepoxide.

In certain embodiments, A is a compound having an alkenyl group and an epoxy group of Formula (3):

where $R^4$ is $C_{1-6}$ alkanediyl; and -A' has the structure of Formula (3a):

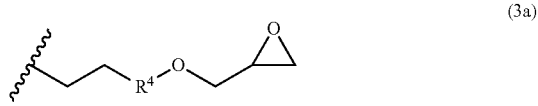

Examples of compounds having two epoxy groups, e.g., a diepoxide, include bisphenol A diglycidyl ether, 1,4-butanediol diglycidyl ether, ethylene glycol diglycidyl ether, neopentyl glycol diglycidyl ether, 1,6-hexanediol diglycidyl ether, 1,4-butane diol diglycidyl ether, and diethylene glycol diglycidyl ether.

Examples of compounds having a Michael acceptor group and an epoxy group include glycidyl (meth)acrylates such as glycidyl acrylate and glycidyl methacrylate, and glycidyl vinyl sulfones.

In certain embodiments of compounds of Formula (1), B represents a core of a z-valent, vinyl-terminated polyfunctional compound B(—V)$_z$ where Z is an integer from 3 to 6. In certain embodiments, polyfunctional compound B(—V)$_z$ has a molecular weight less than 800 Daltons, less than 600 Daltons, less than 400 Daltons and in certain embodiments, less than 200 Daltons. Polyfunctional compounds B(—V)$_z$ in which z is at least 3 may be any of the polyfunctionalizing agents useful in polymer chemistry. In certain embodiments, B(—V)$_z$ is trifunctional and, for example, is selected from triallylcyanurate (TAC), which is reactive with compounds comprising terminal thiol groups, such as 1,2,3-propanetrithiol, which is reactive with terminal allyl groups or vinyl ether groups. Polyfunctionalizing agents having mixed functionality, i.e., agents that include moieties (typically separate moieties), that react with both thiol and vinyl groups, may also be employed. Other useful polyfunctionalizing agents include trimethylolpropane trivinyl ether, and the polythiols described in U.S. Pat. No. 4,366,307, U.S. Pat. No. 4,609,762 and U.S. Pat. No. 5,225,472, each of which is incorporated by reference in its entirety. Combinations of polyfunctionalizing agents having the same terminal groups such as thiol groups or allyl groups may also be used.

In certain embodiments, B represents a core of a z-valent, polyfunctional compound B(—V)$_z$, where z is an integer from 3 to 6. In certain embodiments, z is 3, z is 4, z is 5, and in certain embodiments z is 6. In certain embodiments, a polyfunctional compound is trifunctional. In certain embodiments, a polyfunctional compounds is triallyl cyanurate (TAC) where B has the structure:

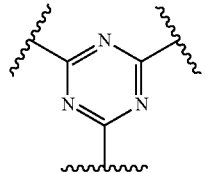 [SMILES: *c1nc(*)nc(*)n1]

and each —V has the structure —O—CH$_2$—CH=CH$_2$.

Each —V is a moiety comprising a terminal group that is reactive with a thiol group such as, for example, an alkenyl group, an epoxy group, or a Michael acceptor group. In certain embodiments, each V is the same, and in certain embodiments, at least one V is different. In certain embodiments —V is selected from $C_{3-8}$ alkene-1-yl and $C_{3-8}$ heteroalkene-1-yl, where the one or more hetero groups is selected from —O— and —S—.

Each —V'— represents a moiety formed by the reaction of a moiety —V with a thiol group. In certain embodiments, V comprises a terminal alkenyl group selected from $C_{3-8}$ alkene-1-yl and $C_{3-8}$ heteroalkene-1-yl, and —V'— is selected from $C_{3-8}$ alkanediyl and $C_{3-8}$ heteroalkanediyl.

In certain embodiments of a compound of Formula (1), B is

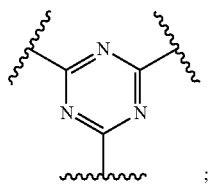 [SMILES: *c1nc(*)nc(*)n1]

each —V'— is —O—$CH_2$—$CH_2$—$CH_2$—; each $R^1$—S—($CH_2$)$_2$—O—($CH_2$)$_2$—O—($CH_2$)$_2$—S—; and each A' is

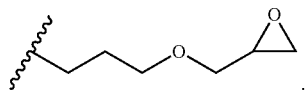 [SMILES: *CCCOCC1CO1]

In certain embodiments, a compound of Formula (1) is 2,2'-[1,2-ethanediylbis(oxy)]bis-ethanethiol (polymer with 2,4,6-tris(2-propen-1-yloxy)-1,3,5-triazine, reaction products with 2-[(2-propen-1-yloxy)methyl]oxirane).

Polyfunctional sulfur-containing epoxies provided by the present disclosure may be used as a curing agent and therefore are intended to have a lower molecular weight than polyfunctional sulfur-containing epoxies forming the bulk of a polymer matrix. For example, polyfunctional sulfur-containing epoxies provided by the present disclosure can have a molecular weight from 500 Daltons to 3,000 Daltons, from 600 Daltons to 2,500 Daltons, from 700 Daltons to 2,000 Daltons, from 800 Daltons to 1,800 Daltons, and, in certain embodiments, from 900 Daltons to 1,500 Daltons.

In certain embodiments, polyfunctional sulfur-containing epoxies provided by the present disclosure comprise the reaction products of reactants comprising: (a) a polyfunctional compound having at least three terminal groups reactive with a thiol group; (b) a dithiol; and (c) an epoxide comprising an epoxy group and a group that is reactive with a thiol group.

In certain embodiment of the reaction, a polyfunctional compound comprises three terminal groups reactive with a thiol group, four terminal groups reactive with a thiol group, five terminal groups reactive with a thiol group, and in certain embodiments, six terminal groups that are reactive with a thiol group. In the reaction, a polyfunctional compound may comprise a polyfunctional compound having a single structure, or in certain embodiments, may comprise a mixture of polyfunctional compounds having different structures and/or functionalities.

In certain embodiments, a polyfunctional compound is trifunctional.

Groups that are reactive with thiol groups include alkenyl groups, epoxy groups, and Michael acceptor groups. A polyfunctional compound may have the same type of groups reactive with a thiol group or at least one of the groups may be different.

A polyfunctional compound can have an average functionality of greater than 3.0, and, in certain embodiments, a value between 3 and 3.5, a value between 3.5 and 4, a value between 3 and 4, a value between 3 and 5, and in certain embodiments, an average value between 3 and 6.

In certain embodiments, a polyfunctional compound is trifunctional, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Publication No. 2010/0010133 at paragraphs [0102]-[0105], the cited portion of which is incorporated herein by reference.

As a result, polyfunctional compounds and polyfunctional sulfur-containing epoxies provided by the present disclosure may have a wide range of average functionality. For example, trifunctionalizing agents combined with a polyfunctional compound of higher functionality may afford average functionalities from 3 to 6, from 3 to 5, from 3 to 4, from 3.0 to 3.5, and in certain embodiments, from 3.0 to 3.25. Wider ranges of average functionality may be achieved by using tetrafunctional or higher functionality polyfunctional compounds. Functionality may be affected and/or determined by factors such as stoichiometry of the reactants, as will be understood by those skilled in the art.

In certain embodiments, dithiols suitable for use in preparing polyfunctional sulfur-containing epoxies include those having Formula (4):

$$HS—R^1—SH \qquad (4)$$

where $R^1$ in Formula (4) denotes a $C_{2-10}$ n-alkanediyl group; a $C_{3-6}$ branched alkanediyl group, which may have one or more pendant groups which may be, for example, hydroxyl groups, alkyl groups, such as methyl or ethyl groups, and/or alkoxy groups; a $C_{6-8}$ cycloalkanediyl group; a $C_{6-10}$ alkanecycloalkanediyl group; a —[(—$CH_2$—)$_p$—X—]$_q$—($CH_2$)$_r$— group, or a —[(—$CH_2$—)$_p$—X—]$_q$—($CH_2$)$_r$— group in which at least one —$CH_2$— unit is substituted with a methyl group, wherein p is an integer having a value ranging from 2 to 6, q is an integer having a value ranging from 1 to 5, r is an integer having a value ranging from 2 to 10, and X represents a heteroatom, such as O, S or another bivalent heteroatom diradical; a secondary or tertiary amine group, i.e., —NR—, where R is selected from hydrogen and methyl; or another substituted trivalent heteroatom. In certain embodiments, X is selected from O and S, and thus $R^1$ in Formula (4) is —[(—$CH_2$—)$_p$—O—]$_q$—($CH_2$)$_r$— or —[(—$CH_2$—)$_p$—S—]$_q$—($CH_2$)$_r$—. In certain embodiments, p and r are equal, such as where p and r are both two, both 3, both 4, both 5, or in certain embodiments, both p and r are 6.

Examples of suitable dithiols include, for example, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A dithiol may have one or more pendant groups selected from a lower (e.g., $C_{1-6}$) alkyl group, a lower alkoxy group, and a hydroxyl group. Suitable alkyl pendant groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in Formula (4), $R^1$ is —[(—CH$_2$—)$_p$—X—]$_q$—(CH$_2$)$_r$—, where p is 2, r is 2, q is 1, and X is —S—); dimercaptodioxaoctane (DMDO) (in Formula (4), $R^7$ is —[(—CH$_2$—)$_p$—X—]$_q$—(CH$_2$)$_r$—, where p is 2, q is 2, r is 2, and X is —O—); and 1,5-dimercapto-3-oxapentane (in Formula (4), $R^1$ is —[(—CH$_2$—)$_p$—X—]$_q$—(CH$_2$)$_r$—, where p is 2, r is 2, q is 1, and X is —O—). It is also possible to use dithiols that include both heteroatoms in the carbon backbone and pendant alkyl groups, such as methyl groups. Such compounds include, for example, methyl-substituted DMDS, such as HS—CH$_2$CH(CH$_3$)—S—CH$_2$CH$_2$—SH, HS—CH(CH$_3$)CH$_2$—S—CH$_2$CH$_2$—SH, and dimethyl substituted DMDS, such as HS—CH$_2$CH(CH$_3$)—S—CHCH$_3$CH$_2$—SH and HS—CH(CH$_3$)CH$_2$—S—CH$_2$CH(CH$_3$)—SH.

A dithiol may include a single type of dithiol such as dithiol of Formula (4) or a combination of different dithiols such as a combination of different dithiols of Formula (4).

In certain embodiments, a dithiol is selected from 1,8-dimercapto-3,6-doxaoctane, and a combination of any of the foregoing. In certain embodiments, a dithiol is 1,8-dimercapto-3,6-doxaoctane.

Suitable epoxides comprising an epoxy group and a group that is reactive with a thiol group include compounds having a terminal epoxy group and a reactive terminal group selected from an alkenyl group, an epoxy group, and a Michael acceptor group.

Suitable epoxides comprising an epoxy group and an alkenyl group include, for example, allyl glycidyl ether, 1,2-epoxy-5-hexene, 1,2-epoxy-7-octene, 1,2-epoxy-9-decene, 4-vinyl-1-cyclohexene 1,2-epoxide, butadiene monoepoxide, isoprene monoepoxide, and limonene monoepoxide. In certain embodiments an epoxide comprising an epoxy group and an alkenyl group has the structure of Formula (3):

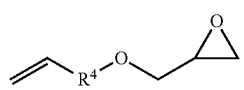

(3)

where $R^4$ is $C_{1-6}$ alkanediyl. In certain embodiments, an epoxide comprising an epoxy group and an alkenyl group is an alkylether epoxy. In certain embodiments, an epoxide comprising an epoxy group and an alkenyl group is allyl glycidyl ether.

Suitable epoxides comprising two epoxy groups include, for example, bisphenol A diglycidyl ether, 1,4-butanediol diglycidyl ether, ethylene glycol diglycidyl ether, neopentyl glycol diglycidyl ether, 1,6-hexanediol diglycidyl ether, 1,4-butane diol diglycidyl ether, and diethylene glycol diglycidyl ether. In certain embodiments, a diepoxide may comprise a polybasic acid-based diepoxy such as in paragraph [0099] of U.S. Publication No. 2009/0326167, which is incorporated herein by reference. Examples of suitable diepoxides include hydantoin diepoxide, diglycidyl ethers of bisphenol-A s, diglycidyl ethers of bisphenol-F, Novalac type epoxides such as DEN-431 (commercially available from Dow Plastics), and epoxidized unsaturated phenolic resins, acrylic polyol esters, methacrylic polyol esters, and triallylcyanurate. Examples of commercially available polybasic acid-based epoxies include Hypox® DA323 (Specialty Chemicals, Inc.), Epotuf® (Reichhold), and Heloxy® (Resolution Performance Products).

Suitable epoxides comprising an epoxy group and a Michael acceptor group include, for example, glycidyl (meth)acrylates such as glycidyl acrylate and glycidyl methacrylate, and glycidyl vinyl sulfones. In certain embodiments, a polyfunctional compound comprises triallyl cyanurate, the dithiol comprises 1,8-dimercapto-3,6-doxaoctane, and the epoxide comprises allyl glycidyl ether. In certain embodiments, a polyfunctional sulfur-containing epoxy is 2,2'-[1,2-ethanediylbis(oxy)]bis-ethanethiol.

Polyfunctional sulfur-containing epoxies provided by the present disclosure are liquid at room temperatures, and in certain embodiments have a viscosity at 25° C. (measured using a CAP2000 viscometer, 25° C., spindle #6 at 50 RPM) from 25 poise to 200 poise, and in certain embodiments, from 50 poise to 150 poise.

Polyfunctional sulfur-containing epoxies provided by the present disclosure may be prepared by first reacting a polyfunctional compound with a dithiol to provide a polyfunctional thiol-terminated intermediate, followed by reaction of the intermediate with an epoxide having an epoxy group and a group that is reactive with a thiol group. The reaction of a polyfunctional compounds and a dithiol can be adapted to the chemistries of the terminal reactive groups. In a second step, a polythiol intermediate can be reacted with an epoxy comprising one epoxy group and a second group that is reactive with a thiol group. The reaction conditions are established such that the polythiol intermediate preferentially reacts with the group that is reactive with the thiol group, and not with the epoxy group, of the monoepoxy. When the monoepoxy comprises a reactive alkenyl group, a polyfunctional sulfur-containing polymer can be the 1:1 addition product of the polythiol intermediate and the monoepoxide. In certain embodiments, a polythiol intermediate and alkenyl monoepoxide can be reacted at a temperature of 70° C. for 1 hour. In certain embodiments, the reaction may be catalyzed by a free-radical catalyst such as, for example, an azo-type catalyst, including Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts are alkyl peroxides, such as t-butyl peroxide.

Thiol-functional intermediates provided by the present disclosure may be prepared, for example, by combining at least one polyfunctional compound B(—V)$_z$ and at least one compound of Formula (4) followed by addition of an appropriate catalyst, and carrying out the reaction at a temperature from 30° C. to 120° C., such as 70° C. to 90° C., for a time from 2 to 24 hours, such as 2 to 6 hours.

Compositions

Compositions provided by the present disclosure comprise a polyfunctional sulfur-containing epoxy. Compositions may contain one or more types of polyfunctional sulfur-containing epoxies and having one or more functionalities of epoxy groups. In certain embodiments, polyfunctional sulfur-containing epoxies are used as curing agents.

In addition to a polyfunctional sulfur-containing epoxy, a composition may include one or more types of difunctional epoxies.

Examples of suitable difunctional epoxies include, for example, polyepoxide resins such as hydantoin diepoxide, diglycidyl ether of bisphenol-A, diglycidyl ether of bisphenol-F, Novolac type epoxides, and any of the epoxidized unsaturated and phenolic resins.

In certain embodiments, a difunctional epoxy contains sulfur, and in certain embodiments, a difunctional epoxy does not contain sulfur.

In certain embodiments, a polyfunctional sulfur-containing epoxy may be used as a curing agent in a composition comprising one or more sulfur-containing polymers.

In certain embodiments, a sulfur-containing polymer is selected from a polythioether, a polysulfide, and a combination thereof. In certain embodiments the sulfur-containing polymer comprises a polythioether, and in certain embodiments, the sulfur-containing polymer comprises a polysulfide. The sulfur-containing polymer may comprise a mixture of different polythioethers and/or polysulfides, and the polythioethers and/or polysulfides may have the same or different functionality. In certain embodiments, the sulfur-containing polymer has an average functionality from 2 to 6, from 2 to 4, from 2 to 3, and in certain embodiments, from 2.05 to 2.5. For example, a sulfur-containing polymer can be selected from a difunctional sulfur-containing polymer, a trifunctional sulfur-containing polymer, and a combination thereof.

In certain embodiments, a sulfur-containing polymer comprises a thiol-terminated polymer such as a thiol-terminated polythioether, a thiol-terminated polysulfide, or a combination thereof.

In certain embodiments, a polyfunctional sulfur-containing epoxy may be used as a curing agent in a composition comprising one or more thiol-terminated polythioethers.

A thiol-terminated polythioether may comprise a mixture of different polythioethers and the polythioethers may have the same or different functionality of thiol groups. In certain embodiments, a thiol-terminated polythioether has an average functionality from 2 to 6, from 2 to 4, from 2 to 3, and in certain embodiments, from 2.05 to 2.5. For example, a thiol-terminated polythioether may be selected from a difunctional sulfur-containing polymer, a trifunctional sulfur-containing polymer, and a combination thereof.

Examples of thiol-functional polythioethers are disclosed, for example in U.S. Pat. No. 6,172,179. In certain embodiments, a thiol-functional polythioether comprises Permapol® P3.1E, available from PRC-DeSoto International Inc., Sylmar, Calif.

In certain embodiments, a thiol-terminated polythioether comprises (a) a backbone comprising a structure having the Formula (5):

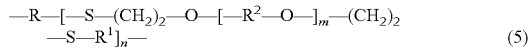   (5)

where (i) each $R^1$ is independently selected from a $C_{2-10}$ n-alkanediyl group, a $C_{3-6}$ branched alkanediyl group, a $C_{6-8}$ cycloalkanediyl e group, a $C_{6-10}$ alkanecycloalkanediyl group, a heterocyclic group, a $—[(—CH_2—)_p—X—]_q—(CH_2)_r—$ group, and a $—[(—CH_2—)_p—X—]_q—(CH_2)_r—$ group in which at least one $—CH_2—$ unit is substituted with a methyl group; (ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a $—[(—CH_2—)_p—X—]_q—(CH_2)_r—$ group; (iii) each X is independently selected from O, S, and a $—NR^6—$ group, in which $R^6$ is selected from hydrogen and a methyl group; (iv) m ranges from 0 to 50; (v) n is an integer from 1 to 60; (vi) p is an integer from 2 to 6; (vii) q is an integer from 1 to 5; and (viii) r is an integer from 2 to 10.

In certain embodiments, a thiol-terminated polythioether is selected from a thiol-terminated polythioether of Formula (6), a thiol-terminated polythioether of Formula (6a), and a combination thereof:

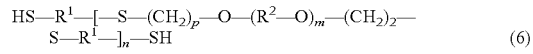   (6)

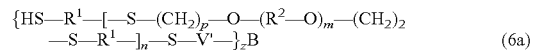   (6a)

where:
each $R^1$ is independently selected from $C_{2-6}$ alkanediyl, $C_{6-8}$ cycloalkanediyl, $C_{6-10}$ alkanecycloalkanediyl, $C_{5-8}$ heterocycloalkanediyl, and $—[(—CHR^3—)_s—X—]_q—(—CHR^3—)_r—$, where:
s is an integer from 2 to 6;
q is an integer from 1 to 5;
r is an integer from 2 to 10;
each $R^3$ is independently selected from hydrogen and methyl; and
each X is independently selected from O, S, and —NHR—, where R is selected from hydrogen and methyl;
each $R^2$ is independently selected from $C_{1-10}$ alkanediyl, $C_{6-8}$ cycloalkanediyl, $C_{6-14}$ alkanecycloalkanediyl, and $—[(—CHR^3—)_s—X—]_q—(—CHR^3—)_r—$, wherein s, q, r, $R^3$, and X are as defined for $R^1$;
m is an integer from 0 to 50;
n is an integer from 1 to 60;
p is an integer from 2 to 6;
B represents a core of a z-valent, a polyfunctional compound B(—V)$_z$ wherein:
z is an integer from 3 to 6; and
each —V is a moiety comprising a terminal group that is reactive with a thiol group; and
each —V'— represents a moiety formed by the reaction of each —V with a thiol group.

In certain embodiments, $R^1$ in Formula (6) and in Formula (6a) is $—[(—CH_2—)_p—X—]_q—(CH_2)_r—$, where p is 2, X is O, q is 2, r is 2, $R^2$ is ethanediyl, m is 2, and n is 9.

Various methods can be used to prepare such polythioethers. Examples of suitable thiol-functional polythioethers, and methods for their production, which are suitable for use in compositions disclosed herein, are described in U.S. Pat. No. 6,172,179 at col. 2, line 29 to col. 4, line 22; col. 6, line 39 to col. 10, line 50; and col. 11, lines 65 to col. 12, line 22, the cited portions of which are incorporated herein by reference. Such thiol-functional polythioethers may be difunctional, that is, linear polymers having two thiol end groups, or polyfunctional, that is, branched polymers have three or more thiol end groups. Suitable thiol-functional polythioethers are commercially available, for example, as Permapol® P3.1E from PRC-DeSoto International Inc., Sylmar, Calif.

Suitable thiol-functional polythioethers may be produced by reacting a divinyl ether or mixtures of divinyl ethers with an excess of dithiol or a mixtures of dithiols. For example, dithiols suitable for use in preparing such thiol-functional polythioethers include those having Formula (4), other dithiols disclosed herein, or combinations of any of the dithiols disclosed herein.

Suitable divinyl ethers include, for example, divinyl ethers having Formula (7):

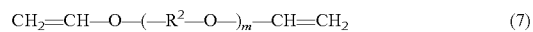   (7)

where $R^2$ in Formula (7) is selected from a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and $—[(—CH_2—)_p—O—]_q—(—CH_2—)_r—$, where p is an integer ranging from 2 to 6, q is an integer from 1 to 5, and r is an integer from 2 to 10. In certain embodiments of a divinyl ether of Formula (7), $R^2$ is a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and in certain embodiments, $-[(-CH_2-)_p-O-]_q-(-CH_2-)_r-$.

Suitable divinyl ethers include, for example, compounds having at least one oxyalkanediyl group, such as from 1 to 4 oxyalkanediyl groups, i.e., compounds in which m in Formula (7) is an integer from 1 to 4. In certain embodiments, m in Formula (7) is an integer ranging from 2 to 4. It is also possible to employ commercially available divinyl ether mixtures that are characterized by a non-integral average value for the number of oxyalkanediyl units per molecule. Thus, m in Formula (7) can also take on rational number values ranging from 0 to 10.0, such as from 1.0 to 10.0, from 1.0 to 4.0, or from 2.0 to 4.0.

Examples of suitable divinyl ethers include, for example, divinyl ether, ethylene glycol divinyl ether (EG-DVE) ($R^2$ in Formula (7) is ethanediyl and m is 1), butanediol divinyl ether (BD-DVE) ($R^2$ in Formula (7) is butanediyl and m is 1), hexanediol divinyl ether (HD-DVE) ($R^2$ in Formula (7) is hexanediyl and m is 1), diethylene glycol divinyl ether (DEG-DVE) ($R^2$ in Formula (4) is ethanediyl and m is 2), triethylene glycol divinyl ether ($R^2$ in Formula (7) is ethanediyl and m is 3), tetraethylene glycol divinyl ether ($R^2$ in Formula (7) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendant groups selected from alkyl groups, hydroxyl groups, alkoxy groups, and amine groups.

In certain embodiments, divinyl ethers in which $R^2$ in Formula (7) is $C_{3-6}$ branched alkanediyl may be prepared by reacting a polyhydroxy compound with acetylene. Examples of divinyl ethers of this type include compounds in which $R^2$ in Formula (7) is an alkyl-substituted methanediyl group such as $-CH(CH_3)-$ (for example Pluriol® blends such as Pluriol®E-200 divinyl ether (BASF Corp., Parsippany, N.J.), for which $R^2$ in Formula (4) is ethanediyl and m is 3.8) or an alkyl-substituted ethanediyl (for example $-CH_2CH(CH_3)-$ such as DPE polymeric blends including DPE-2 and DPE-3 (International Specialty Products, Wayne, N.J.)).

Other useful divinyl ethers include compounds in which $R^2$ in Formula (7) is polytetrahydrofuryl (poly-THF) or polyoxyalkanediyl, such as those having an average of about 3 monomer units.

Two or more types of polyvinyl ether monomers of Formula (7) may be used. Thus, in certain embodiments, two dithiols of Formula (4) and one polyvinyl ether monomer of Formula (7), one dithiol of Formula (4) and two polyvinyl ether monomers of Formula (7), two polythiols of Formula (4) and two divinyl ether monomers of Formula (7), and more than two compounds of one or both formulas, may be used to produce a variety of thiol-functional polythioethers.

In certain embodiments, a polyvinyl ether monomer comprises 20 to less than 50 mole percent of the reactants used to prepare a thiol-functional polythioether, and, in certain embodiments, 30 to less than 50 mole percent.

In certain embodiments provided by the present disclosure, relative amounts of dithiols and divinyl ethers are selected to yield terminal thiol groups. Thus, a dithiol having Formula (4) or a mixture of at least two different dithiols having Formula (4), are reacted with of a divinyl ether having Formula (7) or a mixture of at least two different divinyl ethers having Formula (7) in relative amounts such that the molar ratio of thiol groups to vinyl groups is greater than 1:1, such as 1.1 to 2.0:1.0.

The reaction between compounds of dithiols and divinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. In certain embodiments, the catalyst does not comprise acidic or basic compounds, and does not produce acidic or basic compounds upon decomposition. Examples of free-radical catalysts are an azo-type catalyst, including Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts are alkyl peroxides, such as t-butyl peroxide. The reaction may also be effected by irradiation with ultraviolet light either with or without a cationic photoinitiating moiety.

Thiol-functional polythioethers provided by the present disclosure may be prepared by combining at least one compound of Formula (4) and at least one compound of Formula (7) followed by addition of an appropriate catalyst, and carrying out the reaction at a temperature from 30° C. to 120° C., such as 70° C. to 90° C., for a time from 2 to 24 hours, such as 2 to 6 hours.

As disclosed herein, thiol-terminated polythioethers may comprise a polyfunctional polythioether, i.e., may have an average functionality of greater than 2.0. Suitable polyfunctional thiol-terminated polythioethers include, for example, those having the structure (8):

$$B(-A-SH)_z \qquad (8)$$

wherein: (i) A comprises a structure of Formula (5); (ii) B denotes a z-valent residue of a polyfunctionalizing agent; and (iii) z has an average value of greater than 2.0, and, in certain embodiments, a value between 2 and 3, a value between 2 and 4, a value between 3 and 6, and in certain embodiments, is an integer from 3 to 6.

Polyfunctionalizing agents suitable for use in preparing such polyfunctional thiol-functional polymers include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Publication No. 2010/0010133 at paragraphs [0102]-[0105], the cited portion of which is incorporated herein by reference. Other useful polyfunctionalizing agents include trimethylolpropane trivinyl ether, and the polythiols described in U.S. Pat. Nos. 4,366,307; 4,609,762; and 5,225,472. Mixtures of polyfunctionalizing agents can also be used.

As a result, thiol-functional polythioethers suitable for use in embodiments provided by the present disclosure may have a wide range of average functionality. For example, trifunctionalizing agents may afford average functionalities from 2.05 to 3.0, such as from 2.1 to 2.6. Wider ranges of average functionality may be achieved by using tetrafunctional or higher functionality polyfunctionalizing agents. Functionality may also be affected by factors such as stoichiometry, as will be understood by those skilled in the art.

Thiol-functional polythioethers having a functionality greater than 2.0 may be prepared in a manner similar to the difunctional thiol-functional polythioethers described in U.S. Publication No. 2010/0010133. In certain embodiments, polythioethers may be prepared by combining (i) one or more dithiols described herein, with (ii) one or more divinyl ethers described herein, and (iii) one or more polyfunctionalizing agents. The mixture may then be reacted, optionally in the presence of a suitable catalyst, to afford a thiol-functional polythioether having a functionality greater than 2.0.

Thus, in certain embodiments, a thiol-terminated polythioether comprises the reaction product of reactants comprising:
(a) a dithiol of Formula (4):

$$HS-R^1-SH \qquad (4)$$

wherein:
  $R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and $-[-(CHR^3)_s-X-]_q-(CHR^3)_r-$; wherein:
    each $R^3$ is independently selected from hydrogen and methyl;
    each X is independently selected from $-O-$, $-S-$, $-NH-$, and $-NR-$ wherein R is selected from hydrogen and methyl;
    s is an integer from 2 to 6;
    q is an integer from 1 to 5; and
    r is an integer from 2 to 10; and
(b) a divinyl ether of Formula (7):

$$CH_2=CH-O-[-R^2-O-]_m-CH=CH_2 \qquad (7)$$

wherein:
  each $R^2$ is independently selected from $C_{1-10}$ alkanediyl, $C_{6-8}$ cycloalkanediyl, $C_{6-14}$ alkanecycloalkanediyl, and $-[(-CHR^3-)_s-X-]_q-(-CHR^3-)_r-$, wherein s, q, r, $R^3$, and X are as defined above;
  m is an integer from 0 to 50;
  n is an integer from 1 to 60; and
  p is an integer from 2 to 6.

And, in certain embodiments, the reactants comprise (c) a polyfunctional compound such as a polyfunctional compound $B(-V)_z$.

Thiol-terminated polythioethers provided by the present disclosure represent thiol-terminated polythioethers having a molecular weight distribution. In certain embodiments, thiol-terminated polythioethers useful in compositions can exhibit a number average molecular weight ranging from 500 Daltons to 20,000 Daltons, in certain embodiments, from 2,000 Daltons to 5,000 Daltons, and in certain embodiments, from 3,000 Daltons to 4,000 Daltons. In certain embodiments, thiol-terminated polythioethers useful in compositions provided by the present disclosure exhibit a polydispersity ($M_w/M_n$; weight average molecular weight/number average molecular weight) ranging from 1 to 20, and in certain embodiments, from 1 to 5. The molecular weight distribution of thiol-terminated polythioethers may be characterized by gel permeation chromatography.

In certain embodiments, a sulfur-containing polymer comprises a polysulfide. As used herein, a polysulfide refers to a polymer that contains one or more disulfide linkages, i.e., $-[S-S]-$ linkages, in the polymer backbone and/or in pendant positions on the polymer chain. Often, the polysulfide polymer will have two or more sulfur-sulfur linkages. Suitable polysulfides are commercially available from Akzo Nobel under the tradename Thioplast®. Thioplast® products are available in a wide range of molecular weights ranging, for example, from less than 1,100 to over 8,000, with molecular weight being the average molecular weight in grams per mole. In some cases, the polysulfide has a number average molecular weight of 1,000 to 4,000. The crosslink density of these products also varies, depending on the amount of crosslinking agent used. The —SH content, i.e., thiol or mercaptan content, of these products can also vary. The mercaptan content and molecular weight of the polysulfide can affect the cure speed of the polymer, with cure speed increasing with molecular weight.

In certain embodiments provided by the present disclosure, in addition to or in lieu of, a polysulfide, a composition comprises: (a) from 90 mole percent to 25 mole percent of mercaptan terminated disulfide polymer of the formula $HS(RSS)_mR-SH$; and (b) from 10 mole percent to 75 mole percent of diethyl formal mercaptan terminated polysulfide polymer of the formula $HS(RSS)_nR-SH$, wherein R is $-C_2H_4-O-CH_2-O-C_2H_4-$; R is a divalent member selected from alkyl of from 2 to 12 carbon atoms, alkyl thioether of from 4 to 20 carbon atoms, alkyl ether of from 4 to 20 carbon atoms and one oxygen atom, alkyl ether of from 4 to 20 carbon atoms and from 2 to 4 oxygen atoms each of which is separated from the other by at least 2 carbon atoms, alicyclic of from 6 to 12 carbon atoms, and aromatic lower alkyl; and the value of m and n is such that the diethyl formal mercaptan terminated polysulfide polymer and the mercaptan terminated disulfide polymer have an average molecular weight of from 1,000 Daltons to 4,000 Daltons, such as 1,000 Daltons to 2,500 Daltons. Such polymeric mixtures are described in U.S. Pat. No. 4,623,711 at col. 4, line 18 to col. 8, line 35, the cited portion of which being incorporated herein by reference. In some cases, R in the above formula is $-CH_2-CH_2-$; $-C_2H_4-O-C_2H_4-$; $-C_2H_4-S-C_2H_4-$; $-C_2H_4-O-C_2H_4-O-C_2H_4-$; or $-CH_2-C_6H_4-CH_2-$.

In certain embodiments, a polysulfide comprises a thiol-terminated polysulfide such as those commercially available from Akzo Nobel under the name Thioplast® and from Toray under the name Thiokol®-LP.

In certain embodiments, a composition contains 90% to 150% of the stoichiometric amount, such as 95% to 125% of the stoichiometric amount, of the curing agent(s) such as a polyfunctional sulfur-containing epoxy provided by the present disclosure, a difunctional epoxy, or a combination thereof.

Compositions—Sealants

Compositions provided by the present disclosure may include one or more catalysts.

In certain embodiments, compositions provided by the present disclosure comprise, one or more than one adhesion promoters. A one or more additional adhesion promoter may be present in amount from 0.1 wt % to 15 wt % of a composition, less than 5 wt %, less than 2 wt %, and in certain embodiments, less than 1 wt %, based on the total dry weight of the composition. Examples of adhesion promoters include phenolics, such as Methylon® phenolic resin, and organosilanes, such as epoxy, mercapto or amino functional silanes, such as Silquest® A-187 and Silquest® A-1100. Other useful adhesion promoters are known in the art.

Compositions provided by the present disclosure may comprise one or more different types of filler. Suitable fillers include those commonly known in the art, including inorganic fillers, such as carbon black and calcium carbonate ($CaCO_3$), silica, polymer powders, and lightweight fillers. Suitable lightweight fillers include, for example, those described in U.S. Pat. No. 6,525,168. In certain embodiments, a composition includes 5 wt % to 60 wt % of the filler or combination of fillers, 10 wt % to 50 wt %, and in certain embodiments, from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst.

In certain embodiments, compositions provided by the present disclosure include low density filler particles. As used herein, low density, when used with reference to such particles means that the particles have a specific gravity of no more than 0.7, in certain embodiments no more than 0.25, and in certain embodiments, no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 to 100 microns and a specific gravity of 0.25 (Eccospheres®). Other examples include alumina/silica microspheres having particle sizes in the range of 5 to 300 microns and a specific gravity of 0.7 (Fillite®), aluminum silicate microspheres having a specific gravity of from 0.45 to 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of 40 μm and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). In certain embodiments, compositions provided by the present disclosure include lightweight filler particles comprising an exterior surface coated with a thin coating, such as those described in U.S. Publication No. 2010/0041839 at paragraphs [0016]-[0052], the cited portion of which is incorporated herein by reference.

In certain embodiments, a low density filler comprises less than 2 wt % of a composition, less than 1.5 wt %, less than 1.0 wt %, less than 0.8 wt %, less than 0.75 wt %, less than 0.7 wt % and in certain embodiments, less than 0.5 wt % of a composition, where wt % is based on the total dry solids weight of the composition.

In certain embodiments, compositions provided by the present disclosure comprise at least one filler that is effective in reducing the specific gravity of the composition. In certain embodiments, the specific gravity of a composition is from 0.8 to 1, 0.7 to 0.9, from 0.75 to 0.85, and in certain embodiments, is 0.8. In certain embodiments, the specific gravity of a composition is less than 0.9, less than 0.8, less than 0.75, less than 0.7, less than 0.65, less than 0.6, and in certain embodiments, less than 0.55.

In certain embodiments, a thiol-terminated polythioether including a combination of thiol-terminated polythioethers comprises from 50 wt % to 90 wt % of a composition, from 60 wt % to 90 wt %, from 70 wt % to 90 wt %, and in certain embodiments, from 80 wt % to 90 wt % of the composition, where wt % is based on the total dry solids weight of the composition.

In certain embodiments, a polyfunctional sulfur-containing epoxy comprises from 0.2 wt % to 5 wt % of a composition, from 0.4 wt % to 4 wt %, from 0.6 wt % to 3 wt %, from 0.6 wt % to 2 wt %, from 0.6 wt % to 1.2 wt %, from 0.8 wt % to 2 wt %, and in certain embodiments, from 0.8 wt % to 1.5 wt % of the composition, where wt % is based on the total dry solids weight of the composition.

In certain embodiments, a difunctional epoxy comprises from 1 wt % to 16 wt % of a composition, from 2 wt % to 14 wt %, from 4 wt % to 12 wt %, from 4 wt % to 10 wt %, from 5 wt % to 8 wt %, from 6 wt % to 10 wt %, and in certain embodiments, from 7 wt % to 9 wt % of the composition, where wt % is based on the total dry solids weight of the composition.

In certain embodiments, a composition provided by the present disclosure comprises a polyfunctional sulfur-containing epoxy and a difunctional epoxy. Such compositions may comprise an amount of polyfunctional sulfur-containing epoxy and an amount of difunctional epoxy in any of the respective amounts disclosed herein. In certain embodiments, a composition comprises a ratio (wt %:wt %) of a polyfunctional sulfur-containing epoxy provided by the present disclosure to difunctional epoxy from 1:20 to 1:2, from 1:15 to 1:5, from 1:12 to 1:6, and, in certain embodiments, from 1:10 to 1:7.

A composition may also include any number of additives as desired. Examples of suitable additives include plasticizers, pigments, surfactants, adhesion promoters, thixotropic agents, fire retardants, masking agents, and accelerators (such as amines, including 1,4-diaza-bicyclo[2.2.2]octane, DABCO®), and combinations of any of the foregoing. When used, the additives may be present in a composition in an amount ranging, for example, from 0% to 60% by weight. In certain embodiments, additives may be present in a composition in an amount ranging from 25% to 60% by weight.

Uses

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. In certain embodiments, sealant compositions provided by the present disclosure are useful, e.g., as aerospace sealants and as linings for fuel tanks.

In certain embodiments, compositions, such as sealants, may be provided as multi-pack compositions, such as two-pack compositions, wherein one package comprises one or more thiol-terminated polythioethers provided by the present disclosure and a second package comprises one or more polyfunctional sulfur-containing epoxies provided by the present disclosure. Additives and/or other materials may be added to either package as desired or necessary. The two packages may be combined and mixed prior to use. In certain embodiments, the pot life of the one or more mixed thiol-terminated polythioethers and epoxies is at least 30 minutes, at least 1 hour, at least 2 hours, and in certain embodiments, more than 2 hours, where pot life refers to the period of time the mixed composition remains suitable for use as a sealant after mixing.

Compositions, including sealants, provided by the present disclosure may be applied to any of a variety of substrates. Examples of substrates to which a composition may be applied include metals such as titanium, stainless steel, and aluminum, any of which may be anodized, primed, organic-coated or chromate-coated; epoxy; urethane; graphite; fiberglass composite; Kevlar®; acrylics; and polycarbonates. In certain embodiments, compositions provided by the present disclosure may be applied to a coating on a substrate, such as a polyurethane coating. Compositions provided by the present disclosure may be applied directly onto the surface of a substrate or over an underlayer by any suitable coating process known to those of ordinary skill in the art.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following mixing and application to a surface. In general, full adhesion strength as well as other properties of cured compositions of the present disclosure becomes fully developed within 7 days following mixing and application of a curable composition to a surface.

Cured compositions such as cured sealants exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in JRF for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, the entirety of which is incorporated herein by reference. It is also desirable that when cured, curable compositions of the present disclosure used in aviation and aircraft applications exhibit a percent volume swell not greater than 25% following immersion for one week at 60° C. (140° F.) and ambient pressure in JRF type 1. Other properties, ranges, and/or thresholds may be appropriate for other sealant applications.

For example, in certain embodiments, a cured sealant provided by the present disclosure exhibits a tensile strength of at least 303 psi and an elongation of at least 452%. In certain embodiments, a cured sealant, following immersion in JRF Type I for 7 days at 140° F. exhibits a tensile strength of at least 137 psi and an elongation of at least 252%.

In certain embodiments, compositions provided by the present disclosure are fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28±1% by volume; cyclohexane (technical): 34±1% by volume; isooctane: 38±1% by volume; and tertiary dibutyl disulfide: 1±0.005% by volume (see AMS 2629, issued Jul. 1, 1989, §3.1.1 etc., available from SAE (Society of Automotive Engineers)).

In certain embodiments, compositions provide a cured product, such as a sealant, exhibiting a elongation of at least 100% and a tensile strength of at least 400 psi when measured in accordance with the procedure described in AMS 3279, §3.3.17.1, test procedure AS5127/1, §7.7.

In certain embodiments, compositions provide a cured product, such as a sealant, that exhibits a lap shear strength of greater than 200 psi and in some cases at least 400 psi when measured according to the procedure described in SAE AS5127/1 paragraph 7.8.

In certain embodiments, compositions provided by the present disclosure provide a cured sealant having a lap shear strength of >200 psi, such as at least 220 psi, or, in certain embodiments, at least 250 psi, when measured according to Paragraph 7.8 of AS 5127/1.

In certain embodiments, a cured sealant comprising a composition provided by the present disclosure meets or exceeds the requirements for aerospace sealants as set forth in AMS 3277.

Curable compositions of the present disclosure can exhibit a $T_g$ when cured of −55° C. or less, in certain embodiments, −60° C. or less, and in certain embodiments −65° C. or less. The glass transition temperature, $T_g$, can be measured by differential scanning calorimetry.

In certain embodiments, a cured sealant has a specific gravity less than 2, less than 1.5, less than 1.0, less than 0.8, less than 0.75, less than 0.7, and in certain embodiments, less than 0.5. Furthermore, methods are provided for sealing an aperture utilizing a composition provided by the present disclosure. These methods comprise, for example, applying a composition provided by the present disclosure such as a sealant to a surface to seal an aperture, and curing the composition. In certain embodiments, a method for sealing an aperture comprises (a) applying a sealant composition provided by the present disclosure to one or more surfaces defining an aperture, (b) assembling the surfaces defining the aperture, and (c) curing the sealant, to provide a sealed aperture.

In certain embodiments, a composition may be cured under ambient conditions, where ambient conditions refer to a temperature from 20° C. to 25° C. In certain embodiments, a composition may be cured under conditions encompassing a temperature from a 0° C. to 100° C. In certain embodiments, a composition may be cured at a higher temperature such as at least 30° C., at least 40° C., and in certain embodiments, at least 50° C. In certain embodiments, a composition may be cured at room temperature, e.g., 25° C. In certain embodiments, a composition may be cured upon exposure to actinic radiation such as ultraviolet radiation. As will also be appreciated, the methods may be used to seal apertures on aerospace vehicles including aircraft and aerospace vehicles.

Apertures, including apertures of aerospace vehicles, sealed with compositions provided by the present disclosure are also disclosed.

EXAMPLES

Embodiments provided by the present disclosure are further illustrated by reference to the following examples, which describe the synthesis, properties, and uses of certain polyfunctional sulfur-containing epoxies and compositions comprising such adhesion promoters. It will be apparent to those skilled in the art that many modifications, both to materials, and methods, may be practiced without departing from the scope of the disclosure.

Example 1

Synthesis of Tri-Functional Sulfur-Containing Epoxy

In a 300 mL, 3-necked round bottom flask fitted with a thermal probe, mechanical stirrer, and nitrogen ($N_2$) inlet, 18.8 g of triallyl cyanurate (TAC) and 41.91 g of 1,8-dimercapto-3,6-dioxaoctane (DMDO) were charged, and the mixture was stirred at room temperature for 20 minutes. The mixture was then heated to 70° C., and 16 mg of Vazo®-67 (available from Dupont) was added. The reaction mixture was maintained at 70° C. for 8 hours. The progress of the reaction was monitored by determining the mercaptan equivalent weight (MEW). The final MEW was 297, and the material had a viscosity of 20 poise at 25° C., spindle #6 at 50 RPM, measured using a CAP2000 viscometer.

After this, 39.03 g of allyl glycidyl ether and 246 mg of Vazo®-67 were added. The mixture was maintained at 70° C. for 27 hours and then at 90° C. for 2 hours. A viscous liquid was obtained having a viscosity of 112 poise at 25° C., spindle #6 at 50 RPM, measured using a CAP2000 viscometer.

Example 2

Sealant Formulation

A sealant composition was compounded as follows:
Base Composition:

| Composition | Parts by Weight |
|---|---|
| Polythioethers* | 100 |
| Methylon ® 75108 | 1.4 |
| T-3920** | 0.9 |
| T-3921** | 0.9 |
| Calcium carbonate | 4.5 |
| Carbon black | 7.3 |
| Silica | 10.9 |
| Plasticizer | 2.3 |
| DABCO ® 33-LV | 1.4 |
| Tung oil | 1 |
| Dualite ® E135 | 7.5 |
| Expancel ® 909DET80d15 | 0.6 |
| Tetra N-butyl titanate | 0.6 |
| Acetone | 4.5 |

*Thiol-terminated polythioethers of the type described in U.S. Pat. No. 6,172,179, average thiol functionality: 2.05-2.95, commercially available from PRC-Desoto International, Inc., Sylmar, CA.
**Commercially available from PRC-Desoto International, Inc., Sylmar, CA.

Accelerator Composition:

| Composition | Parts by Weight |
|---|---|
| Epon ® 828 | 88 |
| Example 1 Epoxy | 12 |
| Silica | 10 |
| T-1601** | 3.3 |

**Commercially available from PRC-Desoto International, Inc., Sylmar, CA.

Each of the components of the Base Composition was mixed sequentially in the order listed. In a separate container, each of the components of the Accelerator Composition was mixed sequentially in the order listed. A sealant formulation was prepared by mixing 100 gm of the Base Composition with 8.7 gm of the Accelerator Composition. Tensile strength and elongation were evaluated according to ASTM 3269 and AMS 3276. The die used to prepare the test samples is described in ASTM D 412. The sealant was cured at ambient temperature and humidity. The physical properties of the cured composition and are summarized in Table 1.

TABLE 1

Physical properties of sealant formulations

| Physical Properties | Tensile strength, psi | Elongation, % | Tensile Strength after Immersion*, psi | Elongation after Immersion*, % |
|---|---|---|---|---|
| Example 2 | 303 | 452 | 137 | 252 |
| Comparative Example 3 | 239 | 301 | 142 | 126 |

*Tensile and elongation data was determined after the samples were immersed in Jet Reference Fuel Type I at 140° F. for 7 days.

Example 3

Comparative Sealant Formulation

A comparative sealant composition was compounded as follows:
Base Composition:

| Composition | Parts By Weight |
|---|---|
| Polythioethers* | 100 |
| Methylon ® 75108 | 1.4 |
| T-3920** | 0.9 |
| T-3921** | 0.9 |
| Calcium carbonate | 4.5 |
| Carbon black | 7.3 |
| Silica | 10.9 |
| Plasticizer | 2.3 |
| DABCO ® 33-LV | 1.4 |
| Tung oil | 1 |
| Dualite ® E135 | 7.5 |
| Expancel ® 909DET80d15 | 0.6 |
| Tetra N-butyl titanate | 0.6 |
| Acetone | 4.5 |

*Thiol-terminated polythioethers of the type described in U.S. Pat. No. 6,172,179, average thiol functionality: 2.05-2.95, commercially available from PRC-Desoto International, Inc., Sylmar, CA.
**Commercially available from PRC-Desoto International, Inc., Sylmar, CA.

Accelerator Composition:

| Composition | Parts by Weight |
|---|---|
| Epon ® 828 | 88 |
| DEN ® 438 Epoxy | 12 |
| Silica | 10 |
| T-1601** | 3.3 |

**Commercially available from PRC-Desoto International, Inc., Sylmar, CA.

Each of the components of the Base Composition was mixed sequentially in the order listed. In a separate container, each of the components of the Accelerator Composition was mixed sequentially in the order listed. A sealant formulation according to the present invention was prepared by mixing 100 gm of the Base Composition with 8.7 gm of the Accelerator Composition. Tensile strength and elongation were evaluated according to ASTM 3269 and AMS 3276. The die used to prepare the test samples is described in ASTM D 412. The sealant was cured at ambient temperature and humidity. The physical properties of the cured composition and are summarized in Table 1.

The epoxies in the sealant of Example 2 include a difunctional epoxy, Epon® 828 (bisphenol A diglycidyl ether) and the trifunctional sulfur-containing epoxy of Example 1. The epoxies in the sealant of Example 3 include a difunctional epoxy, Epon® 828 (bisphenol A diglycidyl ether) and an epoxy Novalac resin, DEN 438, which has an average epoxy functionality of 3.6 and does not contain sulfur. As shown in Table, 1, a sealant comprising a polyfunctional sulfur-containing epoxy provided by the present disclosure exhibits a significantly greater elongation following immersion in Jet Reference Fuel Type I at 140° F. for 7 days, than does a sealant comprising a polyfunctional epoxy that does not contain sulfur.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A composition comprising:
   a polyfunctional epoxy comprising the reaction product of reactants comprising:
   (a) a polyfunctional compound having at least three terminal groups reactive with a thiol group;
   (b) a dithiol having the structure of Formula (4):

HS—R$^1$—SH (4)

wherein R$^1$ is —[—(CHR$^3$)$_s$—X—]$_q$—(CHR$^3$)$_r$—; wherein:
   each R$^3$ is independently selected from hydrogen and methyl;
   each X is independently selected from —O— and —S—;
   s is an integer from 2 to 6;
   q is an integer from 1 to 5; and
   r is an integer from 2 to 10; and
   (c) allyl glycidyl ether;
   a difunctional epoxide;
   a combination of thiol-terminated polythioethers characterized by an average functionality from 2.05 to 3; and
   a low density filler.

2. The composition of claim 1, wherein the combination of thiol-terminated polythioethers comprises a thiol-terminated polythioether of Formula (6) and a thiol-terminated polythioether of Formula (6a):

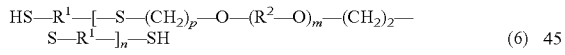

HS—R$^1$—[—S—(CH$_2$)$_p$—O—(R$^2$—O)$_m$—(CH$_2$)$_2$—S—R$^1$—]$_n$—SH (6)

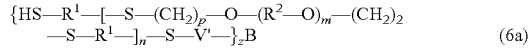

{HS—R$^1$—[—S—(CH$_2$)$_p$—O—(R$^2$—O)$_m$—(CH$_2$)$_2$—S—R$^1$—]$_n$—S—V'—}$_z$B (6a)

wherein:
   each R$^1$ is independently selected from C$_{2-6}$ alkanediyl, C$_{6-8}$ cycloalkanediyl, C$_{6-10}$ alkanecycloalkanediyl, C$_{5-8}$ heterocycloalkanediyl, and —[(—CHR$^3$—)$_s$—X—]$_q$—(—CHR$^3$—)$_r$—, wherein:
   s is an integer from 2 to 6;
   q is an integer from 1 to 5;
   r is an integer from 2 to 10;
   each R$^3$ is independently selected from hydrogen and methyl; and
   each X is independently selected from 0, S, and —NHR—, wherein R is selected from hydrogen and methyl;
   each R$^2$ is independently selected from C$_{1-10}$ alkanediyl, C$_{6-8}$ cycloalkanediyl, C$_{6-14}$ alkanecycloalkanediyl, and —[(—CHR$^3$—)$_s$—X—]$_q$—(—CHR$^3$—)$_r$—, wherein s, q, r, R$^3$, and X are as defined for R$^1$;
   m is an integer from 0 to 50;
   n is an integer from 1 to 60;
   p is an integer from 2 to 6;
   B represents a core of a z-valent, polyfunctional compound B(—V)$_z$ wherein:
   z is an integer from 3 to 6; and
   each —V is a moiety comprising a terminal group that is reactive with a thiol group; and
   each —V'— represents a moiety formed by the reaction of each —V with a thiol group.

3. The composition of claim 1, wherein the combination of thiol-terminated polythioethers comprises the reaction product of reactants comprising:
   (a) a dithiol of Formula (4):

HS—R$^1$—SH (4)

wherein:
   R$^1$ is selected from C$_{2-6}$ alkanediyl, C$_{6-8}$ cycloalkanediyl, C$_{6-10}$ alkanecycloalkanediyl, C$_{5-8}$ heterocycloalkanediyl, and —[—(CHR$^3$)$_s$—X—]$_q$—(CHR$^3$)$_r$—; wherein:
   each R$^3$ is independently selected from hydrogen and methyl;
   each X is independently selected from —O—, —S—, —NH—, and —NR— wherein R is selected from hydrogen and methyl;
   s is an integer from 2 to 6;
   q is an integer from 1 to 5; and
   r is an integer from 2 to 10; and
   (b) a divinyl ether of Formula (7):

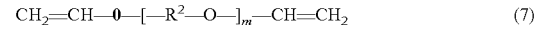

CH$_2$=CH—O—[—R$^2$—O—]$_m$—CH=CH$_2$ (7)

wherein:
   each R$^2$ is independently selected from C$_{1-10}$ alkanediyl, C$_{6-8}$ cycloalkanediyl, C$_{6-14}$ alkanecycloalkanediyl, and —[(—CHR$^3$—)$_s$—X—]$_q$—(—CHR$^3$—)$_r$—, wherein s, q, r, R$^3$, and X are as defined for R$^1$;
   m is an integer from 0 to 50;
   n is an integer from 1 to 60; and
   p is an integer from 2 to 6.

4. The composition of claim 3, wherein the reactants comprise (c) a polyfunctional compound B(—V)$_z$, wherein:
   z is an integer from 3 to 6; and
   each —V is a moiety comprising a terminal group that is reactive with a thiol group.

5. The composition of claim 1, formulated as a sealant.

6. An aperture sealed with the composition of claim 5.

7. A cured sealant, comprising the composition of claim 5.

8. The composition of claim 1, wherein,
   the polyfunctional compound comprises triallyl cyanurate; and
   the dithiol comprises 1,8-dimercapto-3,6-dioxaoctane.

9. The composition of claim 1, wherein the difunctional epoxide comprises bisphenol A diglycidyl ether.

10. The composition of claim 1, wherein,
    the polyfunctional compound comprises triallyl cyanurate;
    the dithiol comprises 1,8-dimercapto-3,6-dioxaoctane;
    the difunctional epoxide comprises bisphenol A diglycidyl ether; and
    the combination of thiol-terminated polythioethers comprises a thiol-terminated polythioether of Formula (6) and a thiol-terminated polythioether of Formula (6a):

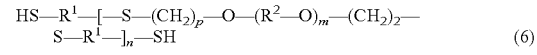

HS—R$^1$—[—S—(CH$_2$)$_p$—O—(R$^2$—O)$_m$—(CH$_2$)$_2$—S—R$^1$—]$_n$—SH (6)

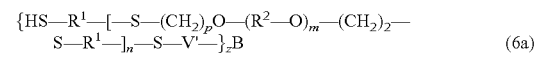

{HS—R$^1$—[—S—(CH$_2$)$_p$O—(R$^2$—O)$_m$—(CH$_2$)$_2$—S—R$^1$—]$_n$—S—V'—}$_z$B (6a)

wherein:
  each $R^1$ is independently selected from $C_{2-6}$ alkanediyl, $C_{6-8}$ cycloalkanediyl, $C_{6-10}$ alkanecycloalkanediyl, $C_{5-8}$ heterocycloalkanediyl, and —[(—CHR³—)$_s$—X—]$_q$—(—CHR³—)$_r$—, wherein:
    s is an integer from 2 to 6;
    q is an integer from 1 to 5;
    r is an integer from 2 to 10;
    each $R^3$ is independently selected from hydrogen and methyl; and
    each X is independently selected from O, S, and —NHR—, wherein R is selected from hydrogen and methyl;
  each $R^2$ is independently selected from $C_{1-10}$ alkanediyl, $C_{6-8}$ cycloalkanediyl, $C_{6-14}$ alkanecycloalkanediyl, and —[(—CHR³—)$_s$—X—]$_q$—(—CHR³—)$_r$—, wherein s, q, r, $R^3$, and X are as defined for $R^1$;
  m is an integer from 0 to 50;
  n is an integer from 1 to 60;
  p is an integer from 2 to 6;
  B represents a core of a z-valent, polyfunctional compound B(—V)$_z$ wherein:
    z is an integer from 3 to 6; and
    each —V is a moiety comprising a terminal group that is reactive with a thiol group; and
  each —V'— represents a moiety formed by the reaction of each —V with a thiol group.

11. The composition of claim 1, wherein the compositions comprises:
  from 0.2 wt % to 5 wt % of the polyfunctional epoxide;
  from 2 wt % to 14 wt % of the difunctional epoxide; and
  from 50 wt % to 90 wt % of the combination of thiol-terminated polythioether,
wherein wt % is based on the total dry weight of the composition.

12. A method of sealing an aperture comprising:
  (a) applying the composition of claim 5 to one or more surfaces defining an aperture;
  (b) assembling the surfaces defining the aperture; and
  (c) curing the sealant to provide the sealed aperture.

* * * * *